(12) United States Patent
Fukagawa et al.

(10) Patent No.: US 12,281,935 B2
(45) Date of Patent: Apr. 22, 2025

(54) DETECTING DEVICE AND MEASURING DEVICE

(71) Applicant: SEIKO EPSON CORPORATION, Tokyo (JP)

(72) Inventors: Takefumi Fukagawa, Fujimi-Machi (JP); Takashi Tajiri, Matsumoto (JP)

(73) Assignee: SEIKO EPSON CORPORATION, Tokyo (JP)

( * ) Notice: Subject to any disclaimer, the term of this patent is extended or adjusted under 35 U.S.C. 154(b) by 112 days.

(21) Appl. No.: 17/975,617

(22) Filed: Oct. 28, 2022

(65) Prior Publication Data
US 2023/0133711 A1 May 4, 2023

(30) Foreign Application Priority Data
Oct. 29, 2021 (JP) .................. 2021-177280

(51) Int. Cl.
*G01J 1/06* (2006.01)
*A61B 5/024* (2006.01)
(Continued)

(52) U.S. Cl.
CPC ............ *G01J 1/06* (2013.01); *A61B 5/02427* (2013.01); *A61B 5/14552* (2013.01); *G01J 3/26* (2013.01);
(Continued)

(58) Field of Classification Search
CPC .... G01J 1/06; G01J 1/0209; G01J 3/26; G01J 3/36; G01J 3/0289; G01J 3/10; G01J 3/0259; G01J 2003/1213; G01J 2003/102; G01J 2003/106; G01J 2001/0257; G01J 2001/061; A61B 5/02427; A61B 5/14552; A61B 5/0059; A61B 5/0075; A61B 5/02; A61B 5/681; A61B 2562/0233
See application file for complete search history.

(56) References Cited

U.S. PATENT DOCUMENTS 8,710,606 B2 * 4/2014 Uematsu ........... H01L 31/02327
257/E31.127
8,976,357 B2 * 3/2015 Uematsu .................... G01J 3/36
359/885
(Continued)

FOREIGN PATENT DOCUMENTS

CN 110268286 9/2019
JP 2012194054 10/2012
(Continued)

*Primary Examiner* — Gordon J Stock, Jr.
(74) *Attorney, Agent, or Firm* — JCIPRNET

(57) ABSTRACT

A detecting device of the present disclosure includes a light emitting portion that emits light and a light receiving portion including an angle limiting member that limits an angle of incidence of light from the light emitting portion, wherein the light receiving portion has a first light receiving region and a second light receiving region that is spaced further from the light emitting portion than the first light receiving region is, the angle limiting member includes a first limiting region corresponding to the first light receiving region and a second limiting region corresponding to the second light receiving region, and the degree of angle limitation of the second limiting region is smaller than the degree of angle limitation of the first limiting region.

11 Claims, 7 Drawing Sheets

(51) Int. Cl.
  *A61B 5/1455* (2006.01)
  *G01J 3/12* (2006.01)
  *G01J 3/26* (2006.01)
  *G01J 3/36* (2006.01)
  *A61B 5/00* (2006.01)

(52) U.S. Cl.
  CPC ............... *G01J 3/36* (2013.01); *A61B 5/681* (2013.01); *A61B 2562/0233* (2013.01); *G01J 2003/1213* (2013.01)

(56) References Cited

U.S. PATENT DOCUMENTS

| | | | | |
|---|---|---|---|---|
| 9,448,111 | B2 * | 9/2016 | Hikmet | G02B 19/0028 |
| 9,709,715 | B2 * | 7/2017 | Nakamura | G01J 3/0289 |
| 9,885,604 | B2 * | 2/2018 | Uematsu | G01J 1/0488 |
| 9,989,640 | B2 * | 6/2018 | Hsu | G01S 7/4813 |
| 10,139,339 | B2 * | 11/2018 | Tschekalinskij | G01J 3/0289 |
| 10,918,322 | B2 | 2/2021 | Shao et al. | |
| 11,600,102 | B2 * | 3/2023 | Tomioka | G02B 5/003 |
| 11,714,002 | B2 * | 8/2023 | Houck | G01J 3/12 |
| | | | | 356/326 |
| 11,714,003 | B2 * | 8/2023 | Houck | G01J 3/0264 |
| | | | | 356/402 |
| 11,872,017 | B2 * | 1/2024 | Tajiri | A61B 5/02444 |
| 11,903,733 | B2 * | 2/2024 | Min | A61B 5/14532 |
| 12,023,153 | B2 * | 7/2024 | Shao | A61B 5/02427 |
| 2012/0236297 | A1 | 9/2012 | Uematsu et al. | |
| 2016/0242659 | A1 * | 8/2016 | Yamashita | A61B 5/02427 |
| 2016/0245700 | A1 * | 8/2016 | Uematsu | H01L 31/02162 |
| 2017/0161544 | A1 * | 6/2017 | Fomani | G01J 1/0488 |
| 2018/0098701 | A1 * | 4/2018 | Blomqvist | A61B 5/021 |
| 2018/0228414 | A1 | 8/2018 | Shao et al. | |
| 2021/0161444 | A1 | 6/2021 | Shao et al. | |
| 2022/0170852 | A1 * | 6/2022 | Yamamoto | A61B 5/1455 |
| 2022/0240822 | A1 * | 8/2022 | Takayama | A61B 5/14552 |
| 2022/0246806 | A1 * | 8/2022 | Yamamoto | H01L 31/0203 |

FOREIGN PATENT DOCUMENTS

| | | | | |
|---|---|---|---|---|
| JP | 2016029374 A | * | 3/2016 | ............ G01J 3/0205 |
| WO | WO-2020226005 A1 | * | 11/2020 | ............ G06K 9/0004 |
| WO | WO-2023085148 A1 | * | 5/2023 | ............ G02B 6/0043 |

* cited by examiner

DETECTING DEVICE AND MEASURING DEVICE

CROSS-REFERENCE TO RELATED APPLICATION

The present application is based on, and claims priority from JP Application Serial Number 2021-177280, filed Oct. 29, 2021, the disclosure of which is hereby incorporated by reference herein in its entirety.

BACKGROUND

1. Technical Field

The present disclosure relates to a detecting device and a measuring device.

2. Related Art

Various measurement technologies for non-invasively measuring biological information such as heartbeats have been proposed in the related art. For example, JP-A-2012-194054 discloses a technology in which, in a detecting device including a light emitting portion that emits light to a living body and a light receiving portion that receives light that is incident thereon by being reflected by the living body after being emitted from the light emitting portion, a spectroscopic filter and an angle limiting filter are provided in the light receiving portion such that stray light transmitted through the spectroscopic filter is blocked by the angle limiting filter.

However, in the above detecting device, the amount of received light varies over the surface of the light receiving portion and thus it has been desired to provide a new technology capable of allowing light to be efficiently incident on the light receiving portion to further improve the detection accuracy.

SUMMARY

An aspect of the present disclosure provides a detecting device including a light emitting unit that emits a light, and a light receiving unit that includes: a sensor having a first light receiving region and a second light receiving region away from the light emitting unit than the first light receiving region, and an angle limiting having a first limiting region corresponding to the first light receiving region and a second limiting region corresponding to the second light receiving region, wherein a degree of angle limitation of the second limiting region is smaller than a degree of angle limitation of the first limiting region.

An aspect of the present disclosure provides a detecting device including a light emitting unit configured to emit light to a living body, a light receiving unit arranged in a first direction with respect to the light emitting unit and configured to receive light from the living body, and a plurality of light shielding walls arranged in the first direction and configured to limit an angle of incidence of light on the light receiving unit, wherein an interval between the light shielding walls in a region far from the light emitting unit is larger than an interval between the light shielding walls in a region close to the light emitting unit.

An aspect of the present disclosure provides a measuring device including the detecting device according to the above aspect and an information analysis unit configured to identify biological information from a detection signal indicating a detection result of the detecting device.

DESCRIPTION OF EXEMPLARY EMBODIMENTS

Hereinafter, embodiments of the present disclosure will be described with reference to the drawings. In each of the following drawings, the scales and angles of members are made different from those of actual ones in order to make the members recognizable in size.

First Embodiment

Figure 1:
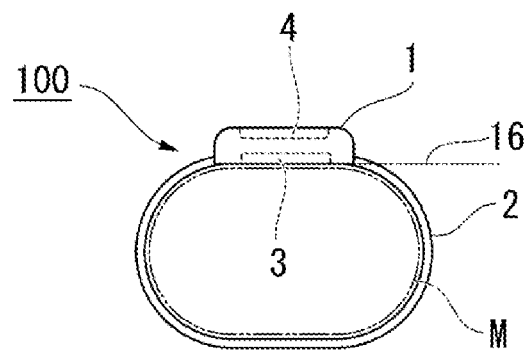
FIG. 1 is a side view of a measuring device of a first embodiment.

FIG. 1 is a side view of a measuring device 100 of a first embodiment. The measuring device 100 of the present embodiment illustrated in FIG. 1 is a biometric device that non-invasively measures biometric information of a subject (for example, a human) which is an example of a living body and is attached to a site (hereinafter referred to as a "measuring site") M that is a measurement target on a body of the subject. The measuring device 100 of the present embodiment is a wristwatch-type portable device including a main body 1 and a belt 2 and can be worn on a wrist of the subject, which is an example of the measuring site (the living body) M, by winding the belt 2 in a band shape around the wrist. In the present embodiment, biological information is exemplified by a heartbeat (for example, a pulse rate) and an oxygen saturation (SpO2) of the subject. The heartbeat indicates the change of the internal volume of a blood vessel over time due to the pulsation of the heart. The oxygen saturation indicates the proportion (%) of hemoglobin bound to oxygen in hemoglobin in the blood of the subject and is an index for evaluating the respiratory function of the subject.

Figure 2:
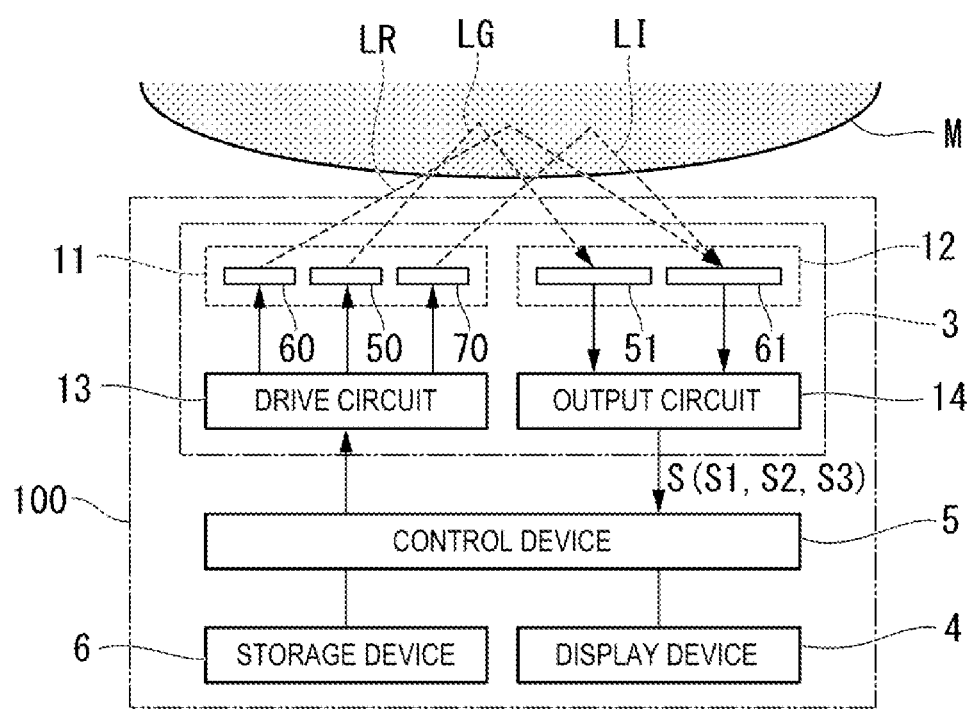
FIG. 2 is a configuration diagram focusing on the functionality of the measuring device.

FIG. 2 is a configuration diagram focusing on the functionality of the measuring device 100. As illustrated in FIG. 2, the measuring device 100 of the present embodiment includes a control device 5, a storage device 6, a display device 4, and a detecting device 3. The control device 5 and the storage device 6 are installed inside the main body 1. As illustrated in FIG. 1, the display device 4 is installed on a surface of the main body 1 opposite to the measuring site M and displays various images including measurement results under the control of the control device 5. The display device 4 is, for example, a liquid crystal display panel.

The detecting device 3 is an optical sensor module that generates detection signals S according to the state of the measuring site M. As illustrated in FIG. 1, the detecting device 3 is installed, for example, on a surface (hereinafter referred to as a detection surface) 16 of the main body 1 that faces the measuring site M. The detection surface 16 is a surface that comes into contact with the measuring site M. As illustrated in FIG. 2, the detecting device 3 of the present embodiment includes a light emitting unit (a light emitting portion) 11, a light receiving unit (a light receiving portion) 12, a drive circuit 13, and an output circuit 14. One or both of the drive circuit 13 and the output circuit 14 can also be installed as circuits external to the detecting device 3. That is, the drive circuit 13 and the output circuit 14 may be omitted from the detecting device 3.

The light emitting unit 11 includes a first light emitting element 50, a second light emitting element 60, and a third light emitting element 70. The first light emitting element 50, the second light emitting element 60, and the third light emitting element 70 are elements that emit light having different wavelengths to the measuring site M.

The first light emitting element 50 emits green light (first light) LG having a green wavelength band of 500 nm to 550 nm toward the measuring site M. The green light LG of the present embodiment is, for example, light having a peak wavelength of 520 nm.

The second light emitting element 60 emits red light (second light) LR having, for example, a red wavelength band of 600 nm to 800 nm toward the measuring site M. The red light LR of the present embodiment is, for example, light having a peak wavelength of 660 nm.

The third light emitting element 70 emits near-infrared light (third light) LI having, for example, a near-infrared wavelength band of 800 nm to 1300 nm toward the measuring site M. The near-infrared light LI of the present embodiment is, for example, light having a peak wavelength of 905 nm.

For example, light emitting diodes (LED) of a bare chip or bullet type are preferably used as light emitting elements that constitute the first light emitting element 50, the second light emitting element 60, and the third light emitting element 70. The wavelengths of light emitted by the light emitting elements are not limited to the above numerical ranges. Hereinafter, the first light emitting element 50, the second light emitting element 60, and the third light emitting element 70 are collectively referred to as "each of the light emitting elements 50, 60, and 70" unless particularly specified.

The drive circuit 13 supplies a drive current to cause each of the light emitting elements 50, 60, and 70 to emit light. The drive circuit 13 of the present embodiment periodically causes each of the light emitting elements 50, 60, and 70 to emit light in a time division manner. Light emitted from the light emitting elements 50, 60, and 70 is incident on the measuring site M and propagates in the measuring site M while being repeatedly reflected and scattered and then is emitted to the main body 1 side, reaching the light receiving unit 12. That is, the detecting device 3 of the present embodiment is a reflection type optical sensor in which the light emitting unit 11 and the light receiving unit 12 are located on one side of the measuring site M.

The light receiving unit 12 receives light arriving from the measuring site M after being emitted by the light emitting unit 11. The light receiving unit 12 of the present embodiment includes a first light receiving element 51 and a second light receiving element 61. The first light receiving element 51 and the second light receiving element 61 generate detection signals according to the intensity of received light. Hereinafter, the first light receiving element 51 and the second light receiving element 61 are collectively referred to as "each of the light receiving elements 51 and 61" unless particularly specified.

The first light receiving element 51 receives green light LG that has propagated in the measuring site M after being emitted from the first light emitting element 50 and generates a detection signal according to the intensity of received light. The second light receiving element 61 receives red light LR that has propagated in the measuring site M after being emitted from the second light emitting element 60 or near-infrared light LI that has propagated in the measuring site M after being emitted from the third light emitting element 70 and generates detection signals according to the intensity of received light.

The output circuit 14 is configured to include, for example, an A/D converter that converts detection signals generated by the light receiving elements 51 and 61 from analog to digital and an amplifier circuit that amplifies the converted detection signals (both not illustrated) and generates a plurality of detection signals S (S1, S2, S3) corresponding to different wavelengths.

The detection signal S1 is a signal indicating the intensity of light received by the first light receiving element 51 when it has received green light LG emitted from the first light emitting element 50. The detection signal S2 is a signal indicating the intensity of light received by the second light receiving element 61 when it has received red light LR emitted from the second light emitting element 60. The detection signal S3 is a signal indicating the intensity of light received by the second light receiving element 61 when it has received near-infrared light LI emitted from the third light emitting element 70.

Each detection signal S is a heartbeat signal including periodic fluctuations corresponding to pulsations (volume heartbeats) of the artery inside the measuring site M because the amounts of absorption by blood during dilation and contraction of blood vessels generally differ.

The drive circuit 13 and the output circuit 14 are mounted on a wiring board in the form of an IC chip together with the light emitting unit 11 and the light receiving unit 12. The drive circuit 13 and the output circuit 14 can be installed outside the detecting device 3 as described above.

The control device 5 is an arithmetic processing unit such as a central processing unit (CPU) or a field-programmable gate array (FPGA) and controls the entirety of the measuring device 100. The storage device 6 includes, for example, a non-volatile semiconductor memory and stores a program executed by the control device 5 and various data used by the control device 5. It is also possible to adopt a configuration in which the functions of the control device 5 are distributed over a plurality of integrated circuits or a configuration in which some or all of the functions of the control device 5 are realized by a dedicated electronic circuit. Although the control device 5 and the storage device 6 are illustrated as separate elements in FIG. 2, a control device 5 including the storage device 6 can also be realized, for example, by an application specific integrated circuit (ASIC).

The control device 5 of the present embodiment identifies biological information of the subject from the plurality of detection signals S (S1, S2, S3) generated by the detecting device 3 by executing the program stored in the storage device 6. Specifically, the control device 5 can identify a pulse-to-pulse interval (PPI) of the subject from the detection signal S1 indicating the intensity of green light LG received by the first light receiving element 51. The control device 5 can also identify the oxygen saturation (SpO2) of the subject by analyzing the detection signal S2 indicating the intensity of red light LR received by the second light receiving element 61 and the detection signal S3 indicating the intensity of near-infrared light LI received by the second light receiving element 61.

In the measuring device 100 of the present embodiment, the control device 5 functions as an information analysis unit that identifies biological information from the detection signals S indicating the detection results of the detecting device 3 as described above. The control device (information analysis unit) 5 causes the display device 4 to display the biological information identified from the detection signals S. It is also possible to notify the user of the measurement result by voice output. It is also preferable to adopt a configuration in which the user is notified of a warning (possibility of impaired physical function) when the pulse rate or oxygen saturation has fluctuated to values out of a predetermined range.

Figure 3:
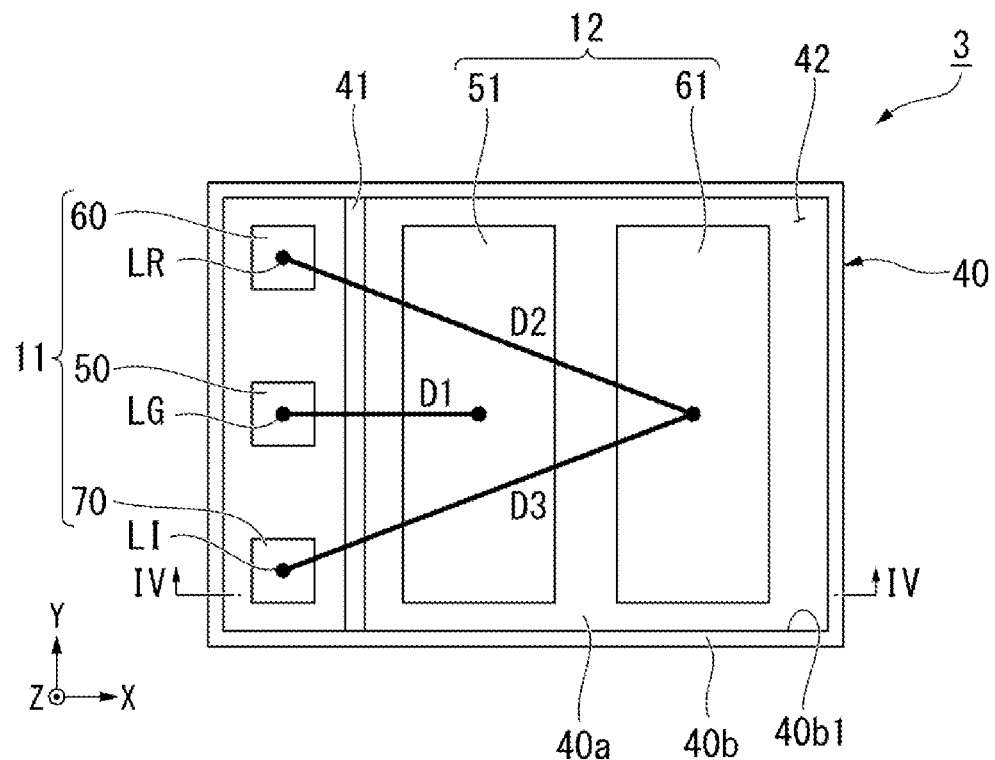
FIG. 3 is a plan view of a detecting device.
Figure 4:
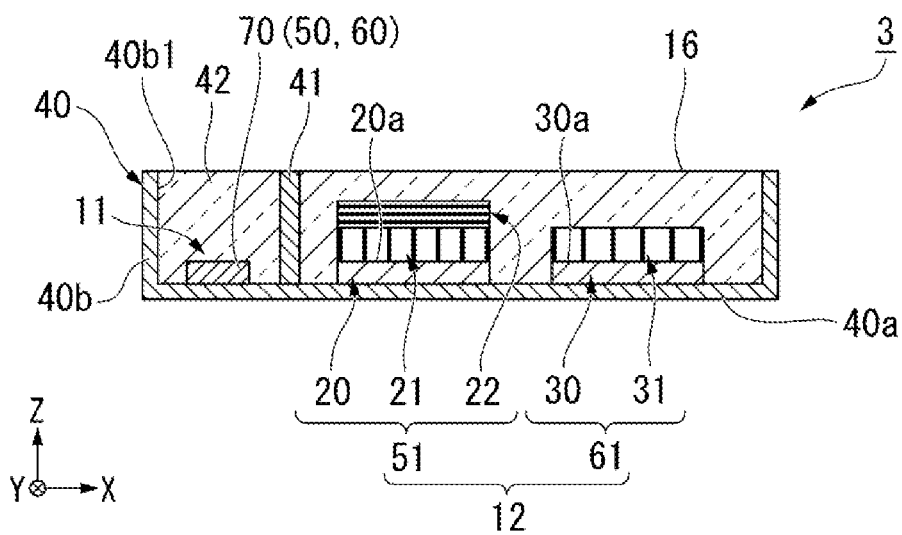
FIG. 4 is a cross-sectional view taken along line IV-IV in FIG. 3.

FIG. 3 is a plan view of the detecting device 3 of the present embodiment. FIG. 4 is a cross-sectional view taken along a line IV-IV in FIG. 3. As illustrated in FIGS. 3 and 4, the detecting device 3 of the present embodiment includes a case 40 and a sealing layer 42 in addition to the light emitting unit 11 and the light receiving unit 12. The drive circuit 13 and the output circuit 14 are not illustrated in FIGS. 3 and 4.

Hereinafter, the configuration of the detecting device 3 will be described using an XYZ coordinate system. The X-axis corresponds to an axis extending along a long side (one side) of the case 40 having a rectangular outer shape, the Y-axis corresponds to an axis that is orthogonal to the X-axis and extends along a short side (another side) of the case 40, and the Z-axis corresponds to an axis that is orthogonal to the X and Y-axes and extends across the thickness of the case 40.

As illustrated in FIGS. 3 and 4, the case 40 is a member that holds the elements of the detecting device 3 (the light emitting unit 11 and the light receiving unit 12). The case 40 is in the shape of a box including a bottom surface portion 40a in the shape of a rectangular flat plate, a frame plate portion 40b in the shape of a rectangular frame that projects to the +Z side from peripheral edges of the bottom surface portion 40a, and a partition wall 41. The case 40 is made of, for example, aluminum. An inner peripheral surface 40b1 of the frame plate portion 40b is colored black to have light blocking properties. This limits reflection on the inner peripheral surface 40b1 of the frame plate portion 40b.

The material and manufacturing method of the case 40 are arbitrary. For example, the case 40 can be formed by injection molding of a resin material. It is also preferable to adopt a configuration in which the case 40 is integrally formed with the main body 1.

The light emitting unit 11 and the light receiving unit 12 are installed on the bottom surface portion 40a of the case 40 while being mounted on a wiring board (not illustrated). In the case 40, the light emitting unit 11 and the light receiving unit 12 are arranged in the X-axis direction (a first direction).

The partition wall 41 is a plate-shaped member that protrudes to the +Z side from the bottom surface portion 40a and extends in the Y-axis direction and separates the internal accommodation space of the case 40 into two parts in the X-axis direction. That is, the partition wall 41 is a member that separates the space accommodating the light emitting unit 11 and the light receiving unit 12 in a direction along the X axis. The partition wall 41 is a member having light blocking properties for blocking light emitted from the light emitting unit 11 such that it is not directly incident on the light receiving unit 12. It can also be said that the partition wall 41 is a member that blocks a part of the green light LG, the red light LR, and the near-infrared light LI.

The sealing layer 42 is a light-transmitting resin material filled in a gap between the frame plate portion 40b and the light emitting and receiving units 11 and 12 accommodated in the case 40. In the present embodiment, the sealing layer 42 seals the light emitting elements 50, 60, and 70 and the light receiving elements 51 and 61. The sealing layer 42 seals (molds) the light emitting and receiving units 11 and 12 in the case 40. In the present embodiment, an upper surface of the sealing layer 42 is flush with upper surfaces of the frame plate portions 40b and 41 of the case 40. The surface of the sealing layer 42 functions as the detection surface 16.

The light emitting unit 11 is installed in the case 40 such that the light emitting surfaces of the light emitting elements 50, 60, and 70 are parallel to the XY plane. That is, the light emitting elements 50, 60, and 70 emit light toward the +Z side.

The light receiving unit 12 is installed in the case 40 such that the light receiving surfaces of the light receiving elements 51 and 61 are parallel to the XY plane. That is, the light receiving elements 51 and 61 receive light incident from the Z direction.

As illustrated in FIG. 3, the light emitting elements 50, 60, and 70 are arranged side by side at intervals in the Y-axis direction (a second direction) orthogonal to (intersecting) the X-axis direction. Specifically, the second light emitting element 60 is arranged on the +Y side of the first light emitting element 50 and the third light emitting element 70 is arranged on the −Y side of the first light emitting element 50. That is, the first light emitting element 50 is arranged between the second light emitting element 60 and the third light emitting element 70 in the direction along the Y axis. It can also be said that the first light emitting element 50 is located between the second light emitting element 60 and the third light emitting element 70.

The light receiving elements 51 and 61 are arranged side by side at intervals in the X-axis direction intersecting (orthogonal to) the Y axis. Specifically, the first light receiving element 51 is arranged on the +X side of the light emitting unit 11 and the second light receiving element 61 is arranged on the +X side of the first light receiving element 51. That is, the second light receiving element 61 is arranged on a side of the first light receiving element 51 opposite to the light emitting unit 11.

Here, let D1 be a distance from the first light emitting element 50 to the first light receiving element 51, D2 a distance from the second light emitting element 60 to the second light receiving element 61, and D3 a distance from the third light emitting element 70 to the second light receiving element 61. The distance D1 corresponds to the distance between central portions of the first light emitting element 50 and the first light receiving element 51 when viewed in plan in the Z-axis direction. The distance D2 corresponds to the distance between central portions of the second light emitting element 60 and the second light receiving element 61 when viewed in plan in the Z-axis direction. The distance D3 corresponds to the distance between central portions of the third light emitting element 70 and the second light receiving element 61 when viewed in plan in the Z-axis direction.

In the detecting device 3 of the present embodiment, the distance D1 from the first light emitting element 50 to the first light receiving element 51 is shorter than the distance D2 from the second light emitting element 60 to the second light receiving element 61. The distance D1 from the first light emitting element 50 to the first light receiving element 51 is also shorter than the distance D3 from the third light emitting element 70 to the second light receiving element 61. The distance D2 and the distance D3 are equal.

As described above, the detecting device 3 of the present embodiment adopts a configuration in which the first light receiving element 51 for receiving green light LG is arranged at a position closest to the first light emitting element 50 that emits the green light LG. That is, the first light receiving element 51 is provided closer to the light emitting unit 11 than the second light receiving element 61 is in the X-axis direction in which the light emitting unit 11 and the light receiving unit 12 are arranged.

As illustrated in FIG. 4, the first light receiving element 51 includes a sensor 20, a first angle limiting filter (angle limiting member) 21, and a bandpass filter 22.

The sensor 20 includes, for example, a photodiode (PD). The first angle limiting filter 21 is provided to cover the entirety of a light receiving surface 20a of the sensor 20.

The first angle limiting filter 21 has a property of transmitting light incident at an angle smaller than a predetermined incident angle and blocking light incident at an angle larger than the predetermined incident angle without transmitting the light. Thus, the first angle limiting filter 21 can limit the angle of incidence of light on the sensor 20.

Specifically, the first angle limiting filter 21 transmits light which is incident at a predetermined incident angle (hereinafter referred to as an allowable incident angle) due to having propagated in the living body and guides it to the sensor 20 and blocks light which is incident at an angle larger than the allowable incident angle, such as external light such as sunlight or light which has not entered the living body, to prevent it from being incident on the sensor 20. That is, the first angle limiting filter 21 is an angle limiting member that limits the angle of incidence of green light LG from the first light emitting element 50 with respect to the sensor 20. Details of the configuration of the first angle limiting filter 21 will be described later.

The bandpass filter 22 has a property of selectively transmitting the wavelength band of green light LG and absorbing and blocking red light LR and near-infrared light LI which are light of other wavelength bands. The bandpass filter 22 is formed, for example, by alternately laminating low refractive index layers such as silicon oxide layers and high refractive index layers such as titanium oxide layers on the first angle limiting filter 21.

For example, a part of red light LR and near-infrared light LI emitted from the second and third light emitting elements 60 and 70 may pass through the living body and enter the first light receiving element 51. In the case of the present embodiment, the first light receiving element 51 includes the bandpass filter 22 that selectively transmits green light LG. Therefore, the first light receiving element 51 can block red light LR and near-infrared light LI having wavelength bands different from that of green light LG. Thus, the first light receiving element 51 can efficiently receive green light LG emitted from the first light emitting element 50.

The second light receiving element 61 includes a sensor 30 that receives red light LR or near-infrared light LI and a second angle limiting filter (angle limiting member) 31 that limits the angle of incidence of red light LR or near-infrared light LI that reaches the sensor 30. That is, in the detecting device 3 of the present embodiment, the second light receiving element 61 differs from the first light receiving element 51 in that it does not include a bandpass filter that selectively transmits red light LR or near-infrared light LI.

The sensor 30 includes, for example, a photodiode. The second angle limiting filter 31 is provided to cover the entirety of a light receiving surface 30a of the sensor 30. The second angle limiting filter 31 can limit the angle of incidence of red light LR or near-infrared light LI that reaches the sensor 30.

For example, the second angle limiting filter 31 transmits red light LR or near-infrared light LI which is incident at an allowable incident angle after propagating in the living body and guides it to the sensor 30 and blocks light which is incident at an angle larger than the allowable incident angle, such as external light such as sunlight or red light LR or near-infrared light LI which has not passed through the living body, to prevent it from being incident on the sensor 30. That is, the second angle limiting filter 31 is an angle limiting member that limits the angle of incidence, with respect to the sensor 30, of red light LR or near-infrared light LI from the second light emitting element 60 or the third light emitting element 70. Details of the configuration of the second angle limiting filter 31 will be described later.

Figure 5:
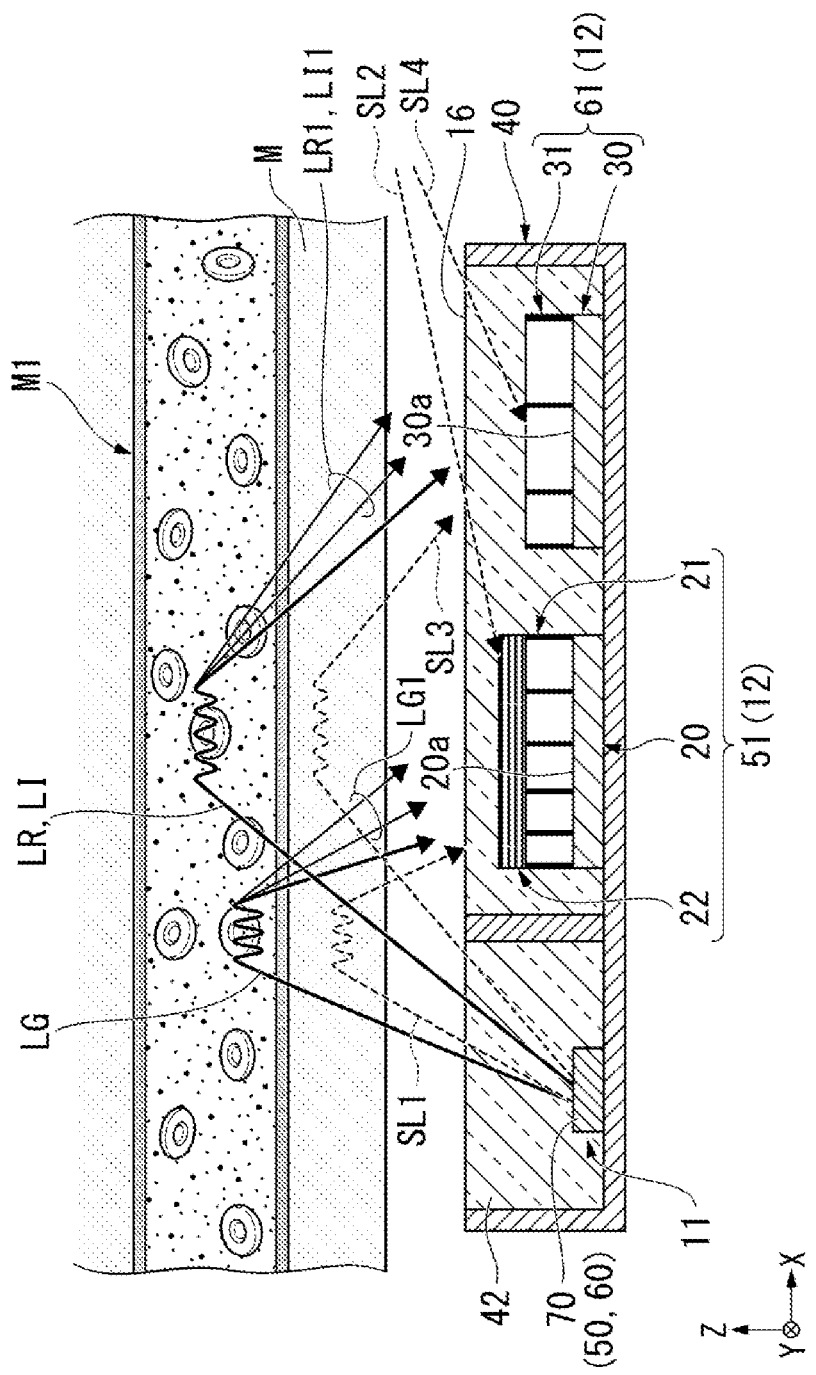
FIG. 5 is a diagram illustrating the behavior of light emitted from a light emitting unit.

FIG. 5 is a diagram illustrating the behavior of light emitted from the light emitting unit 11.

As illustrated in FIG. 5, for example, a part of green light LG emitted from the first light emitting element 50 may be reflected by a surface layer of the living body (the measuring site M), such that it is directly incident on the first light receiving element 51 without reaching the blood vessel M1 inside the living body. External light such as sunlight may also be directly incident on the first light receiving element 51 through a gap between the living body and the detection surface 16.

Green light LG that is directed to the first light receiving element 51 without reaching the blood vessel M1 is referred to as a "first stray light component SL1" and external light that is directed directly to the first light receiving element 51 is referred to as a "second stray light component SL2".

Because the first stray light component SL1 has a green wavelength band, it passes through the bandpass filter 22 and is incident on the first angle limiting filter 21 provided in a layer below the bandpass filter 22. The first angle limiting filter 21 has a property of transmitting light incident at an angle smaller than the allowable incident angle and blocking light incident at an angle larger than the allowable incident angle as described above.

Because the first stray light component SL1 is incident on the first light receiving element 51 without reaching the blood vessel M1, the angle of incidence of the first stray light component SL1 with respect to the first light receiving element 51 is larger than the allowable incident angle of the first angle limiting filter 21. That is, the first stray light component SL1 is blocked by the first angle limiting filter 21. Thus, the first light receiving element 51 can limit the incidence of the first stray light component SL1 on the light receiving surface 20a of the sensor 20 through the first angle limiting filter 21.

The second stray light component SL2 is mostly blocked by the bandpass filter 22, but a component having a green wavelength band included in the second stray light component SL2 passes through the bandpass filter 22. Here, the angle of incidence of the second stray light component SL2 with respect to the first light receiving element 51 is larger than the allowable incident angle of the first angle limiting filter 21 because the second stray light component SL2 is incident through the gap between the living body and the detection surface 16 as described above. Therefore, a part of the second stray light component SL2 (a component having a green wavelength band) transmitted through the bandpass filter 22 is blocked by the first angle limiting filter 21. Thus, the first light receiving element 51 can limit the incidence of the second stray light component SL2 on the light receiving surface 20a of the sensor 20 through the first angle limiting filter 21.

On the other hand, green light LG that has propagated in the blood vessel M1 passes through the bandpass filter 22 and is incident on the first angle limiting filter 21 provided in the layer below the bandpass filter 22 at a predetermined angle. Because the green light LG that has propagated in the blood vessel M1 is emitted from the inside of the living body, it is incident on the first light receiving element 51 at a smaller incident angle, that is, at an angle closer to the normal direction, compared to the first stray light component SL1 reflected on the surface layer of the living body.

The allowable incident angle of the angle limiting filter is generally designed to be smaller than the angle of incidence of light that has propagated in the blood vessel with respect to the light receiving unit. The angle limiting filter is formed, for example, by embedding light shielding walls made of a light blocking material such as tungsten in a light-transmitting silicon oxide layer using a semiconductor process. In the related art, a general angle limiting filter has been configured by embedding light shielding walls arranged at equal intervals in a silicon oxide layer.

Based on simulations, the present inventor has found that light that has passed through the living body cannot be efficiently incident on the light receiving surface of the sensor of the light receiving unit when an angle limiting filter of the related art in which light-shielding walls are embedded in a silicon oxide layer at equal intervals is used.

In a light receiving element using an angle limiting filter in which light shielding walls are embedded at equal intervals as in the configuration of the related art, a light incident region in which green light LG is mostly incident is formed on the light receiving surface near the first light emitting element 50 and the amount of received green light LG incident on the light receiving surface decreases away from the first light emitting element 50. That is, the amount of light received by the light receiving element varies over the surface when the angle limiting filter of the related art in which light shielding walls are embedded at equal intervals is used.

Figure 6:
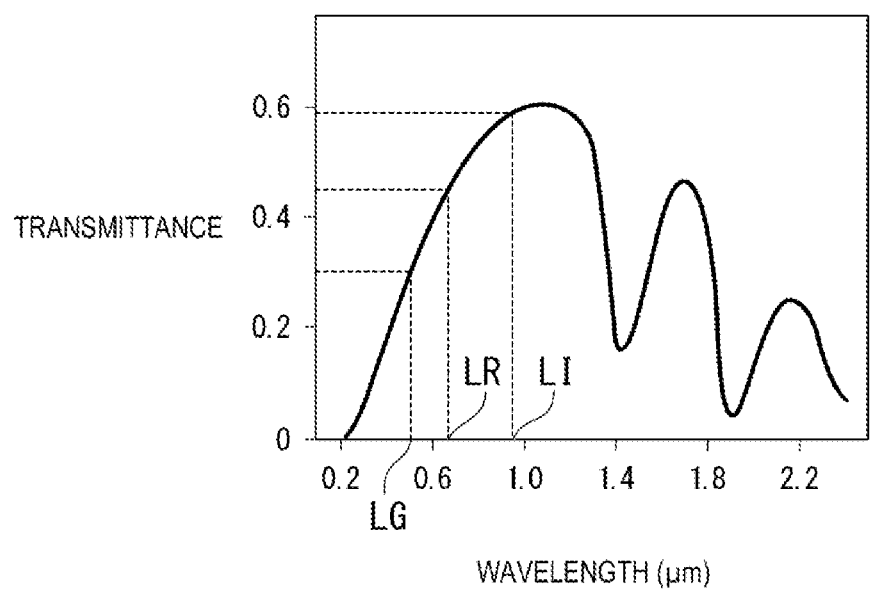
FIG. 6 is a graph showing a transmission spectrum of a skin.

FIG. 6 is a graph showing a transmission spectrum of the skin. In FIG. 6, the horizontal axis represents the wavelength of light and the vertical axis represents the transmittance (in percentage). FIG. 6 shows a transmission spectrum when the skin thickness is 0.43 mm as an example.

As shown in FIG. 6, the transmittance is about 30% when the wavelength band of green light LG (for example, 520 nm) is incident on the skin, about 50% to 60% when the wavelength band of red light LR (for example, 660 nm) is incident on the skin, and about 60% when the wavelength band of near-infrared light LI (for example, 905 nm) is incident on the skin.

The graph of FIG. 6 shows that the distance that light can propagate in the living body differs depending on the wavelength of light. That is, according to the graph of FIG. 6, it can be seen that green light LG can propagate only a short distance in the living body, compared to red light LR or near-infrared light LI. That is, it can be said that red light LR and near-infrared light LI can propagate further in the living body than green light LG. Although FIG. 6 illustrates the case where the skin thickness is 0.43 mm as an example, red light LR and near-infrared light LI can also propagate further in the living body with other skin thicknesses than green light LG.

The present inventor has found that green light LG is more likely to be attenuated when passing through a living body than red light LR and near-infrared light LI are as shown in the graph of FIG. 6. Thus, the present inventor has thought that, in a light receiving element using an angle limiting filter in which light shielding walls are embedded at equal intervals as in the related art, the likelihood that green light LG is attenuated in the living body before it is incident on the light receiving surface increases away from the first light emitting element 50, and as a result, the amount of received light varies over the light receiving surface in the X-axis direction away from the first light emitting element 50.

Therefore, the present inventor has focused on the structure of the angle limiting filter and completed the detecting device 3 of the present embodiment which can limit variations in the amount of received light over the light receiving element.

Figure 7:
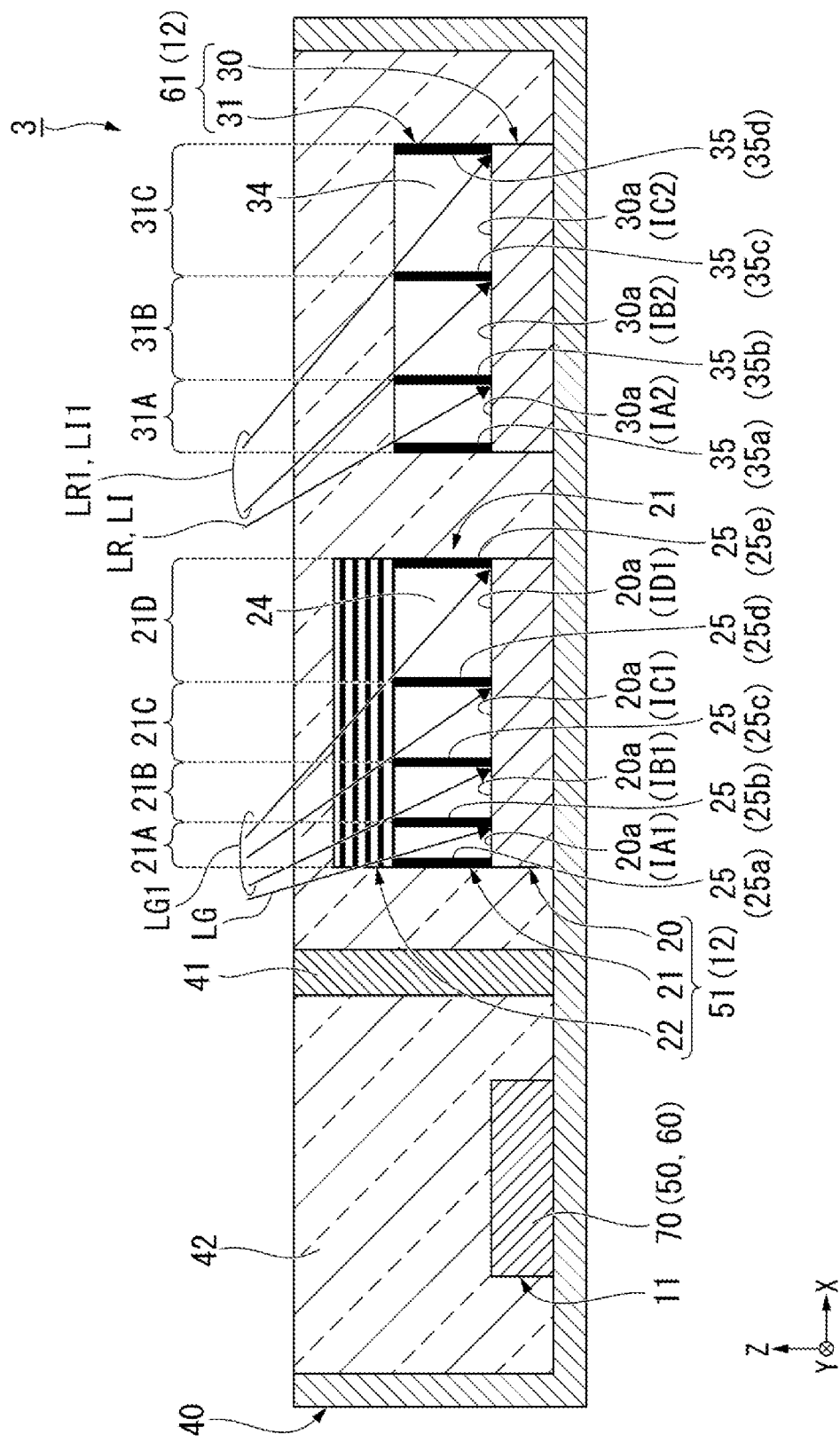
FIG. 7 is a cross-sectional view illustrating a configuration of a main part of the detecting device of the first embodiment.

FIG. 7 is a cross-sectional view illustrating a configuration of a main part of the detecting device 3 of the present embodiment.

As illustrated in FIG. 7, the first light receiving element 51 has a plurality of light receiving regions. The plurality of light receiving regions include a first light receiving region IA1, a second light receiving region IB1, a third light receiving region IC1, and a fourth light receiving region ID1. Hereinafter, the first light receiving region IA1, the second light receiving region IB1, the third light receiving region IC1, and the fourth light receiving region ID1 are collectively referred to as "each of the light receiving regions IA1, IB1, IC1, and ID1" unless particularly specified.

The light receiving regions IA1, IB1, IC1, and ID1 are provided on the light receiving surface 20a of the sensor 20 of the first light receiving element 51. Specifically, the first light receiving region IA1 is a region which is located closest to the light emitting unit 11 (located on the most −X side) in the light receiving surface 20a of the sensor 20. The second light receiving region IB1 is a region that is spaced further from the light emitting unit 11 to the +X side than the first light receiving region IA1 is, the third light receiving region IC1 is a region that is spaced further from the light emitting unit 11 to the +X side than the second light receiving region IB1 is, and the fourth light receiving region ID1 is a region that is spaced further from the light emitting unit 11 to the +X side than the third light receiving region IC1 is. That is, the light receiving regions IA1, IB1, IC1 and ID1 are arranged on the light receiving surface 20a one by one on the +X side in this order.

The first angle limiting filter 21 includes a first limiting region 21A, a second limiting region 21B, a third limiting region 21C, and a fourth limiting region 21D. Hereinafter, the first limiting region 21A, the second limiting region 21B, the third limiting region 21C, and the fourth limiting region 21D are collectively referred to as "each of the limiting regions 21A, 21B, 21C, and 21D" unless particularly specified.

The limiting regions 21A, 21B, 21C, and 21D correspond respectively to the light receiving regions IA1, IB1, IC1, and ID1.

The first limiting region 21A is arranged to overlap the first light receiving region IA1 when viewed in plan from the +Z side and limits the angle of incidence of the green light LG with respect to the first light receiving region IA1 of the first light receiving element 51.

The second limiting region 21B is arranged to overlap the second light receiving region IB1 when viewed in plan from the +Z side and limits the angle of incidence of the green light LG with respect to the second light receiving region IB1 of the first light receiving element 51.

The third limiting region 21C is arranged to overlap the third light receiving region IC1 when viewed in plan from the +Z side and limits the angle of incidence of the green light LG with respect to the third light receiving region IC1 of the first light receiving element 51.

The fourth limiting region 21D is arranged to overlap the fourth light receiving region ID1 when viewed in plan from the +Z side and limits the angle of incidence of the green light LG with respect to the fourth light receiving region ID1 of the first light receiving element 51.

In the present embodiment, the degree of angle limitation of the second limiting region 21B is smaller than the degree of angle limitation of the first limiting region 21A. The degree of angle limitation of the third limiting region 21C is smaller than the degree of angle limitation of the second limiting region 21B. The degree of angle limitation of the fourth limiting region 21D is smaller than the degree of angle limitation of the third limiting region 21C.

That is, in the detecting device 3 of the present embodiment, the degree of angle limitation of each of the limiting regions 21A, 21B, 21C, and 21D progressively decreases away from the first light emitting element 50.

Here, the degree of angle limitation being "small" indicates that light incident on the first light receiving element 51 at a large incident angle (a shallow angle] away from the vertical direction) can reach the light receiving surface 20a of the sensor 20, i.e., that the allowable incident angle is large.

On the other hand, the degree of angle limitation being "large" indicates that light incident on the first light receiving element 51 at a small incident angle (a steep angle close to the vertical direction) can reach the light receiving surface 20a of the sensor 20, i.e., that the allowable incident angle is small.

The first angle limiting filter 21 includes a silicon oxide layer 24 and a plurality of light shielding walls (first light shielding walls) 25 embedded in the silicon oxide layer 24. Each of the light shielding walls 25 is formed in a plate shape extending to the +Z side from the light receiving surface 20a of the sensor 20. Although omitted in FIG. 7, the plurality of light shielding walls 25 are arranged not only in the X-axis direction but also in the Y-axis direction such that they form a grid shape as a whole when viewed in plan from the +Z side.

The first angle limiting filter 21 is formed, for example, by embedding light shielding walls 25 made of conductive plugs having light absorptivity such as tungsten plugs in a silicon oxide layer 24 through a wiring forming process of a semiconductor process. The silicon oxide layer 24 forms an optical path for guiding light to the light receiving surface 20a of the sensor 20. The light shielding walls 25 embedded in the silicon oxide layer 24 limit the angle of incidence of light passing through the optical path (the silicon oxide layer 24). That is, when light incident on the silicon oxide layer 24 is tilted more than a predetermined angle with respect to the optical path, the incident light hits a light shielding wall 25 and a part of the light is absorbed by the light shielding wall 25 while the rest is reflected. Because the intensity of the reflected light is weakened due to repeated reflections while the light passes through the optical path, light that can completely pass through the first angle limiting filter 21 is substantially limited to light whose inclination with respect to the optical path is within a predetermined limiting angle.

Based on such a configuration, the first angle limiting filter 21 functions as an angle limiting member that limits the angle of incidence of green light LG from the first light emitting element 50 with respect to the sensor 20.

In the first angle limiting filter 21 of the present embodiment, the plurality of light shielding walls 25 are provided on the light receiving regions IA1, IB1, IC1, and ID1 of the first light receiving element 51. The plurality of light shielding walls 25 include light shielding walls 25a, 25b, 25c, 25d, and 25e.

The light shielding walls 25a and 25b define the first limiting region 21A in the X-axis direction. The light shielding walls 25b and 25c define the second limiting region 21B in the X-axis direction. The light shielding walls 25c and 25d define the third limiting region 21C in the X-axis direction. The light shielding walls 25d and 25e define the fourth limiting region 21D in the X-axis direction.

The degrees of angle limitation of the limiting regions 21A, 21B, 21C, and 21D are defined by the X-axis intervals between adjacent light shielding walls.

In the present embodiment, the plurality of light shielding walls that limit the angle of incidence of light on the light receiving unit 12 are arranged in the X-axis direction such that the interval between light shielding walls in a region far from the light emitting unit 11 is larger than the interval between light shielding walls in a region close to the light emitting unit 11. Specifically, the X-axis interval between the adjacent light shielding walls 25b and 25c in the second limiting region 21B among the plurality of light shielding walls 25 is larger than the X-axis interval between the adjacent light shielding walls 25a and 25b in the first limiting region 21A among the plurality of light shielding walls 25.

The X-axis interval between the adjacent light shielding walls 25c and 25d in the third limiting region 21C among the plurality of light shielding walls 25 is larger than the X-axis interval between the adjacent light shielding walls 25b and 25c in the second limiting region 21B among the plurality of light shielding walls 25.

The X-axis interval between the adjacent light shielding walls 25d and 25e in the fourth limiting region 21D among the plurality of light shielding walls 25 is larger than the X-axis interval between the adjacent light shielding walls 25c and 25d in the third limiting region 21C among the plurality of light shielding walls 25.

In the case of the present embodiment, for example, the interval between the light shielding walls 25a and 25b is set to 3 μm, the interval between the light shielding walls 25b and 25c is set to 4.5 μm, the interval between the light shielding walls 25c and 25d is set to 6 μm, and the interval between the light shielding walls 25d and 25e is set to 7.5 μm. The heights of the light shielding walls 25a, 25b, 25c, 25d, and 25e are set to 5 μm.

The allowable incident angle of the second limiting region 21B is larger than the allowable incident angle of the first limiting region 21A because the second limiting region 21B has a larger interval in the X-axis direction than the first limiting region 21A as illustrated in FIG. 7.

In the first angle limiting filter 21 of the present embodiment, the X-axis intervals between adjacent light shielding walls are adjusted as described above such that the degree of angle limitation of the second limiting region 21B is smaller than the degree of angle limitation of the first limiting region 21A.

The allowable incident angle of the third limiting region 21C is larger than the allowable incident angle of the second limiting region 21B because the third limiting region 21C has a larger interval in the X-axis direction than the second limiting region 21B.

In the first angle limiting filter 21 of the present embodiment, the X-axis intervals between adjacent light shielding walls are adjusted as described above such that the degree of angle limitation of the third limiting region 21C is smaller than the degree of angle limitation of the second limiting region 21B.

The allowable incident angle of the fourth limiting region 21D is larger than the allowable incident angle of the third limiting region 21C because the fourth limiting region 21D has a larger interval in the X-axis direction than the third limiting region 21C.

In the first angle limiting filter 21 of the present embodiment, the X-axis intervals between adjacent light shielding walls are adjusted as described above such that the degree of angle limitation of the fourth limiting region 21D is smaller than the degree of angle limitation of the third limiting region 21C.

The first light receiving element 51 of the present embodiment is provided with the first angle limiting filter 21 such that the degree of angle limitation (the allowable incident angle) of the first light receiving element 51 decreases toward the +X side away from the first light emitting element 50 as described above.

Green light LG that has propagated in the blood vessel M1 is emitted from the living body while being scattered as illustrated in FIG. 5. Therefore, green light LG that has propagated in the blood vessel M1 has scattering components. A part of the scattering components includes scattering components LG1 directed to the +X side of specular reflection components from the living body.

The scattering components LG1 have a larger angle of incidence with respect to the first light receiving element 51 than the specular reflection components of green light LG that are emitted after propagating in the blood vessel M1. That is, the scattering components LG1 have a larger inclination with respect to the normal direction of the light receiving surface 20a of the sensor 20.

Therefore, in the case of an angle limiting filter in which light shielding walls are embedded at equal intervals, the degree of angle limitation is constant in the X-axis direction, such that the scattering components LG1 having a larger angle of incidence than the specular reflection components of the green light LG are blocked by the light shielding walls and cannot be incident on the light receiving surface 20a of the sensor 20.

On the other hand, in the first angle limiting filter 21 of the present embodiment, the degree of angle limitation of the first light receiving element 51 (the light receiving surface 20a of the sensor 20) decreases toward the +X side. That is, the first light receiving element 51 has a larger allowable incident angle on the +X side than on the −X side, such that it can transmit even the scattering components LG1 having a large inclination with respect to the normal direction of the light receiving surface 20a of the sensor 20.

The first angle limiting filter 21 can allow the scattering components LG1 to be incident on the light receiving surface 20a of the sensor 20, for example, via the third limiting region 21C or the fourth limiting region 21D having a relatively large allowable incident angle.

According to the first light receiving element 51 of the present embodiment, the first angle limiting filter 21 whose degree of angle limitation decreases toward the +X side away from the first light emitting element 50 is provided, such that it is possible to inject the scattering components LG1, which are blocked by the angle limiting filter of the related art, into the sensor 20. Thus, the first light receiving element 51 reduces variations in the amount of received light over the light receiving surface 20a of the sensor 20 and efficiently injects green light LG emitted from the light emitting unit 11 into the sensor 20, thus achieving high detection accuracy.

Here, in the detecting device 3 of the present embodiment, a part of the red light LR emitted from the second light emitting element 60 or a part of the near-infrared light LI emitted from the third light emitting element 70 may be directly incident on the second light receiving element 61 without passing through the living body as illustrated in FIG. 5. External light such as sunlight may also be directly incident on the second light receiving element 61 through the gap between the living body and the detection surface 16. Hereinafter, red light LR or near-infrared light LI that is directed directly to the second light receiving element 61 without passing through the living body is collectively referred to as a "third stray light component SL3" and external light that is directed directly to the second light receiving element 61 is referred to as a "fourth stray light component SL4".

Because the third stray light component SL3 is incident on the second angle limiting filter 31 without passing through the living body, the angle of incidence of the third stray light component SL3 with respect to the second light receiving element 61 is larger than the allowable incident angle of the second angle limiting filter 31. Because the fourth stray light component SL4 is incident through the gap between the living body and the detection surface 16, the angle of incidence of the fourth stray light component SL4 with respect to the second light receiving element 61 is larger than the allowable incident angle of the second angle limiting filter 31.

Therefore, the third stray light component SL3 and the fourth stray light component SL4 are satisfactorily blocked by the second angle limiting filter 31. Thus, the second light receiving element 61 can limit the incidence of the third stray light component SL3 and the fourth stray light component SL4 on the light receiving surface 30a of the sensor 30 through the second angle limiting filter 31.

The second light receiving element 61 is configured similar to the first light receiving element 51.

The second light receiving element 61 has a plurality of light receiving regions including a first light receiving region IA2, a second light receiving region IB2, and a third light receiving region IC2. Hereinafter, the first light receiving region IA2, the second light receiving region IB2, and the third light receiving region IC2 are collectively referred to as "each of the light receiving regions IA2, IB2, and IC2" unless particularly specified.

Each of the light receiving regions IA2, IB2, and IC2 corresponds to a part of the light receiving surface 30a of the sensor 30 of the second light receiving element 61. The light receiving regions IA2, IB2, and IC2 are arranged on the light receiving surface 30a one by one on the +X side in this order.

In the present embodiment, the number (3) of light receiving regions of the second light receiving element 61 differs from the number (4) of light receiving regions of the first light receiving element 51.

The second angle limiting filter 31 is configured similar to the first angle limiting filter 21. The second angle limiting filter 31 includes a first limiting region 31A, a second limiting region 31B, and a third limiting region 31C. Hereinafter, the first limiting region 31A, the second limiting region 31B, and the third limiting region 31C are collectively referred to as "each of the limiting regions 31A, 31B, and 31C" unless particularly specified.

The limiting regions 31A, 31B, and 31C correspond respectively to the light receiving regions IA2, IB2, and IC2.

The first limiting region 31A is arranged to overlap the first light receiving region IA2 when viewed in plan from the +Z side and limits the angle of incidence of the red light LR or the near-infrared light LI with respect to the first light receiving region IA2 of the second light receiving element 61.

The second limiting region 31B is arranged to overlap the second light receiving region IB2 when viewed in plan from the +Z side and limits the angle of incidence of the red light LR or the near-infrared light LI with respect to the second light receiving region IB2 of the second light receiving element 61.

The third limiting region 31C is arranged to overlap the third light receiving region IC2 when viewed in plan from the +Z side and limits the angle of incidence of the red light LR or the near-infrared light LI with respect to the third light receiving region IC2 of the second light receiving element 61.

In the detecting device 3 of the present embodiment, the degree of angle limitation of each of the limiting regions 31A, 31B, and 31C progressively decreases away from the light emitting elements 60 and 70.

The second angle limiting filter 31 includes a silicon oxide layer 34 and a plurality of light shielding walls (second light shielding walls) 35 embedded in the silicon oxide layer 34. Each light shielding wall 35 is formed in a plate shape extending to the +Z side from the light receiving surface 30a of the sensor 30. Although omitted in FIG. 7, the plurality of light shielding walls 35 are arranged not only in the X-axis direction but also in the Y-axis direction such that they form a grid shape as a whole when viewed in plan from the +Z side.

The second angle limiting filter 31 is formed through a wiring forming process of a semiconductor process similar to that of the first angle limiting filter 21.

The plurality of light shielding walls 35 include light shielding walls 35a, 35b, 35c, and 35d.

The light shielding walls 35a and 35b define the first limiting region 31A in the X-axis direction. The light shielding walls 35b and 35c define the second limiting region 31B in the X-axis direction. The light shielding walls 35c and 35d define the third limiting region 31C in the X-axis direction. The degrees of angle limitation of the limiting regions 31A, 31B, and 31C are defined by the X-axis intervals between adjacent light shielding walls.

In the present embodiment, the X-axis interval between the adjacent light shielding walls 35b and 35c in the second limiting region 31B among the plurality of light shielding walls 35 is larger than the X-axis interval between the adjacent light shielding walls 35a and 35b in the first limiting region 31A among the plurality of light shielding walls 35.

The X-axis interval between the adjacent light shielding walls 35c and 35d in the third limiting region 31C among the plurality of light shielding walls 35 is larger than the X-axis interval between the adjacent light shielding walls 35b and 35c in the second limiting region 31B among the plurality of light shielding walls 35.

In the case of the present embodiment, for example, the interval between the light shielding walls 35a and 35b is set to 4.5 µm, the interval between the light shielding walls 35b and 35c is set to 6 µm, and the interval between the light shielding walls 35c and 35d is set to 7.5 µm. The heights of the light shielding walls 35a, 35b, 35c, and 35d are set to 5 µm.

The second light receiving element 61 of the present embodiment is provided with the second angle limiting filter 31 such that the degree of angle limitation (the allowable incident angle) of the second light receiving element 61 decreases toward the +X side away from the light emitting elements 60 and 70 as illustrated in FIG. 7.

Here, the light emitting elements 50, 60, and 70 (the light emitting unit 11) that emit green light LG, red light LR, and near-infrared light LI are arranged at the same position in the X-axis direction, while the second light receiving element 61 that receives red light LR or near-infrared light LI is arranged at a position spaced to the +X side further than the first light receiving element 51 that receives green light LG is as illustrated in FIG. 5.

Thus, the second light receiving element 61 is arranged at a position spaced further from the light emitting unit 11 in the X-axis direction than the first light receiving element 51 is, such that the angle of incidence of red light LR or near-infrared light LI with respect to the second light receiving element 61 is larger than the angle of incidence of green light LG with respect to the first light receiving element 51.

In the case of the present embodiment, the degree of angle limitation of the first limiting region 31A in the second angle limiting filter 31 is smaller than the degree of angle limitation of the first limiting region 21A in the first angle limiting filter 21. Specifically, the X-axis interval between the adjacent light shielding walls 35a and 35b in the first limiting region 31A is larger than the X-axis interval between the adjacent light shielding walls 25a and 25b in the first limiting region 21A.

That is, the allowable incident angle of the first limiting region 31A in the second angle limiting filter 31 is larger than the allowable incident angle of the first limiting region 21A in the first angle limiting filter 21. Making the allowable incident angle of the first limiting region 31A located on the light emitting unit 11 side in the second angle limiting filter 31 larger relative to that of the first limiting region 21A in the first angle limiting filter 21 in this manner ensures that red light LR or near-infrared light LI that is incident at a larger angle with respect to the second light receiving element 61 can be incident on the light receiving surface 30a of the sensor 30 without being blocked as described above.

Because red light LR or near-infrared light LI that have propagated in the blood vessel M1 is emitted from the living body while being scattered as illustrated in FIG. 5, the red light LR or near-infrared light LI has scattering components. A part of the scattering components includes scattering components LR1 and LI1 directed to the +X side of specular reflection components from the living body.

The scattering components LR1 and LI1 have a larger incident angle with respect to the second light receiving element 61 than the specular reflection components of red light LR or near-infrared light LI that are emitted after propagating in the blood vessel M1.

In the second angle limiting filter 31 of the present embodiment, the degree of angle limitation of the second light receiving element 61 (the light receiving surface 30a of the sensor 30) decreases toward the +X side, such that the allowable incident angle on the +X side is larger than the allowable incident angle on the −X side.

Thus, the second angle limiting filter 31 can allow the scattering components LR1 and LI1 to be incident on the light receiving surface 30a of the sensor 30, for example, via the second limiting region 31B or the third limiting region 31C which is located on the +X side and has a relatively large allowable incident angle.

According to the second light receiving element 61 of the present embodiment, the second angle limiting filter 31 whose degree of angle limitation decreases toward the +X side away from the light emitting elements 60 and 70 is provided, such that it is possible to inject the scattering components LR1 and LI1, which are blocked by the angle limiting filter of the related art, into the sensor 30.

Thus, the second light receiving element 61 reduces variations in the amount of received light over the light receiving surface 30a of the sensor 30, such that red light LR or near-infrared light LI emitted from the light emitting unit 11 is efficiently injected into the sensor 30, thus achieving high detection accuracy.

Further, in the detecting device 3 of the present embodiment, the distance D1 between the first light emitting element 50 and the first light receiving element 51 is smaller than the distance between the second light emitting element 60 or the third light emitting element 70 and the second light receiving element 61 (the distance D2 or D3).

In the case of the present embodiment, the first light receiving element 51 is arranged at a position closest to the first light emitting element 50, such that it can efficiently receive green light LG that is incident on the first light receiving element 51 after propagating in the living body. Red light LR and near-infrared light LI can propagate further in the living body than the green light LG as described above. Therefore, the second light receiving element 61 can efficiently receive the red light LR and the near-infrared light LI that have propagated a longer distance in the living body than the green light LG.

Thus, the detecting device 3 of the present embodiment can accurately detect green light LG, red light LR, and near-infrared light LI that have propagated in the living body through the light receiving unit 12.

In the detecting device 3 of the present embodiment, the distance that the red light LR and the near-infrared light LI propagates in the living body until they are incident on the second light receiving element 61 is larger than the distance that the green light LG propagates in the living body until it is incident on the first light receiving element 51.

The green light LG can propagate only a short distance in the living body, compared to the red light LR or the near-infrared light LI as described above. Therefore, if the green light LG propagates in the living body such that it can reach the second light receiving element 61, the green light LG is sufficiently attenuated while passing through the living body. Thus, the green light LG cannot be incident on the second light receiving element 61.

On the other hand, the red light LR and the near-infrared light LI can propagate further in the living body than the green light LG. Therefore, even when the red light LR and the near-infrared light LI have propagated a longer distance in the living body than the green light LG, a sufficient amount of the red light LR and the near-infrared light LI can be incident on the second light receiving element 61 spaced further from the light emitting unit 11.

In the case of the present embodiment, only the red light LR and the near-infrared light LI are incident on the second light receiving element 61, such that it is not necessary to provide the second light receiving element 61 with a band pass filter that selectively transmits the red light LR and the near-infrared light LI and blocks the green light LG. That is, the detecting device 3 of the present embodiment can adopt the above configuration in which only the first light receiving element 51 includes the bandpass filter 22 while the second light receiving element 61 does not include a bandpass filter. Thus, the detecting device 3 of the present embodiment can omit a bandpass filter for the second light receiving element 61, reducing the cost.

The first light receiving element 51 of the present embodiment can make it difficult for the first stray light component SL1 and the second stray light component SL2 to be incident on the light receiving surface 20a of the sensor 20. Thus, the first light receiving element 51 can limit the incidence of the first stray light component SL1 and the second stray light component SL2, which are noise components, achieving a high S/N ratio.

The second light receiving element 61 of the present embodiment can also make it difficult for the third stray light component SL3 and the fourth stray light component SL4 to be incident on the light receiving surface 30a of the sensor 30. Thus, the second light receiving element 61 can limit the incidence of the third stray light component SL3 and the fourth stray light component SL4, which are noise components, achieving a high S/N ratio.

The detecting device 3 of the present embodiment can greatly improve the detection accuracy of the light receiving unit 12 by increasing the amount of received light while increasing the S/N ratio as described above. Thus, the detecting device 3 of the present embodiment enables highly accurate light reception by the light receiving elements 51 and 61, such that it is possible to reduce power consumption of the light emitting unit 11 by limiting the amount of light emission from the light emitting elements 50, 60 and 70.

The measuring device 100 of the present embodiment includes the above detecting device 3 and thus can provide a biometric measuring device capable of highly accurate detection while reducing power consumption.

Second Embodiment

Subsequently, a detecting device of a second embodiment will be described. The detecting device of the present embodiment differs from that of the first embodiment in the configurations of the first and second angle limiting filters which are angle limiting members. Hereinafter, the same reference numerals will be used for the components and members common with the first embodiment and reference numerals will be omitted for details.

Figure 8:
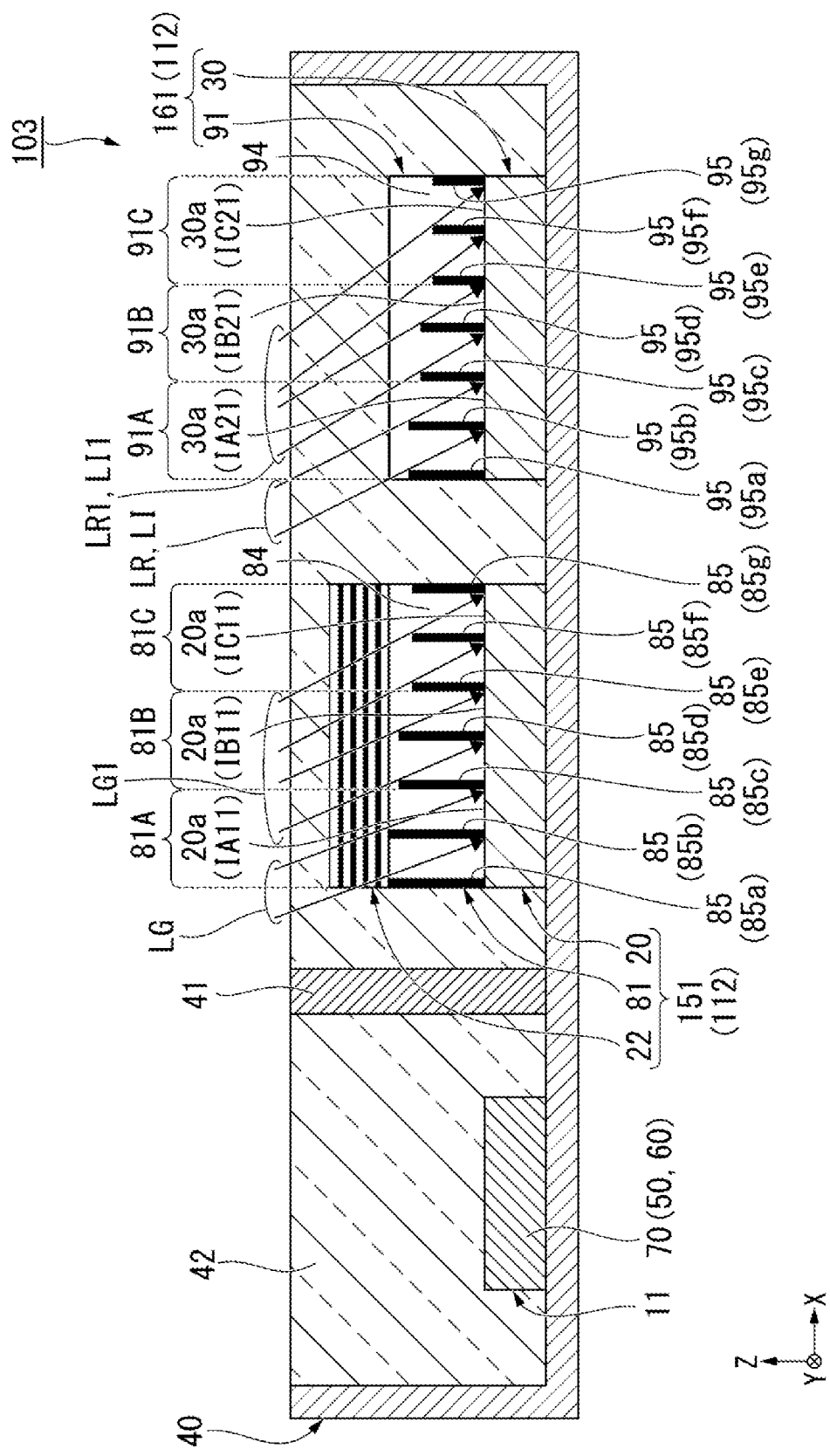
FIG. 8 is a cross-sectional view illustrating a configuration of a main part of a detecting device of a second embodiment.

FIG. 8 is a cross-sectional view illustrating a configuration of a main part of a detecting device 103 of the present embodiment.

As illustrated in FIG. 8, the detecting device 103 of the present embodiment includes a light emitting unit 11, a light receiving unit 112, a case 40, and a sealing layer 42. The light receiving unit 112 of the present embodiment includes a first light receiving element 151 and a second light receiving element 161.

The first light receiving element 151 includes a sensor 20, a first angle limiting filter (angle limiting member) 81, and a bandpass filter 22. The second light receiving element 161 includes a sensor 30 and a second angle limiting filter (angle limiting member) 91.

In the detecting device 103 of the present embodiment, the first light receiving element 151 includes a first light receiving region IA11, a second light receiving region IB11, and a third light receiving region IC11. Hereinafter, the first light receiving region IA11, the second light receiving region IB11, and the third light receiving region IC11 are collectively referred to as "each of the light receiving regions IA11, IB11, and IC11" unless particularly specified.

Each of the light receiving regions IA11, IB11, and IC11 corresponds to a part of the light receiving surface 20a of the sensor 20 of the first light receiving element 151. The light receiving regions IA11, IB11, and IC11 are arranged on the light receiving surface 20a of the sensor 20 one by one on the +X side in this order.

The first angle limiting filter 81 includes a first limiting region 81A, a second limiting region 81B, and a third limiting region 81C. Hereinafter, the first limiting region 81A, the second limiting region 81B, and the third limiting region 81C are collectively referred to as "each of the limiting regions 81A, 81B, and 81C" unless particularly specified.

The limiting regions 81A, 81B, and 81C correspond respectively to the light receiving regions IA11, IB11, and IC11. In the detecting device 103 of the present embodiment, the degree of angle limitation of each of the limiting regions 81A, 81B, and 81C progressively decreases away from the first light emitting element 50.

The first angle limiting filter 81 includes a silicon oxide layer 84 and a plurality of light shielding walls (first light shielding walls) 85 embedded in the silicon oxide layer 84. In the first angle limiting filter 81, the plurality of light shielding walls 85 are provided on the light receiving regions IA11, IB11, and IC11 of the first light receiving element 151. The plurality of light shielding walls 85 include light shielding walls 85a, 85b, 85c, 85d, 85e, 85f, and 85g.

The light shielding wall 85a and the light shielding wall 85b are arranged in the X-axis direction in the first limiting region 81A. In the case of the present embodiment, the heights of the light shielding walls 85a and 85b are set to, for example, 5 μm.

The light shielding wall 85c and the light shielding wall 85d are arranged in the X-axis direction in the second limiting region 81B. In the case of the present embodiment, the heights of the light shielding walls 85c and 85d are set to, for example, 4 μm.

The light shielding wall 85e, the light shielding wall 85f, and the light shielding wall 85g are arranged in the X-axis direction in the third limiting region 81C. In the case of the present embodiment, the heights of the light shielding walls 85e, 85f, and 85g are set to, for example, 3 μm.

The X-axis intervals between adjacent ones of the light shielding walls 85a, 85b, 85c, 85d, 85e, 85f, and 85g are set to, for example, 3 μm.

The first angle limiting filter 81 of the present embodiment can be formed, for example, by providing portions in which conductive plugs such as tungsten plugs having light absorptivity are embedded and portions in which no conductive plugs are embedded through multiple steps into which a wiring forming process of a semiconductor process is divided, such that a plurality of light shielding walls 85 with different heights are embedded in the silicon oxide layer 24.

In the case of the present embodiment, the degrees of angle limitation of the limiting regions 81A, 81B, and 81C are defined by the heights of light shielding walls arranged in the X-axis direction.

In the present embodiment, the height of the light shielding walls 85c and 85d arranged in the X-axis direction in the second limiting region 81B among the plurality of light shielding walls 85 is less than the height of the light shielding walls 85a and 85b arranged in the X-axis direction in the first limiting region 81A among the plurality of light shielding walls 85.

The height of the light shielding walls 85e, 85f, and 85g arranged in the X-axis direction in the third limiting region 81C among the plurality of light shielding walls 85 is also less than the height of the light shielding walls 85c and 85d arranged in the X-axis direction in the second limiting region 81B among the plurality of light shielding walls 85.

The allowable incident angle of the second limiting region 81B is larger than the allowable incident angle of the first limiting region 81A because the height of the light shielding walls of the second limiting region 81B is less than that of the first limiting region 81A as illustrated in FIG. 8.

In the first angle limiting filter 81 of the present embodiment, the heights of light shielding walls arranged in the X-axis direction are adjusted as described above such that the degree of angle limitation of the second limiting region 81B is smaller than the degree of angle limitation of the first limiting region 81A.

The allowable incident angle of the third limiting region 81C is larger than the allowable incident angle of the second limiting region 81B because the height of the light shielding walls of the third limiting region 81C is less than that of the second limiting region 81B.

In the first angle limiting filter 81 of the present embodiment, the heights of light shielding walls arranged in the X-axis direction are adjusted as described above such that the degree of angle limitation of the third limiting region 81C is smaller than the degree of angle limitation of the second limiting region 81B.

The first light receiving element 151 of the present embodiment is provided with the first angle limiting filter 81 such that the degree of angle limitation (the allowable incident angle) of the first light receiving element 151 decreases toward the +X side away from the first light emitting element 50 as described above.

The first angle limiting filter 81 of the present embodiment can allow the scattering components LG1 to be incident on the light receiving surface 20a of the sensor 20, for example, via the second limiting region 81B or the third limiting region 81C having a relatively large allowable incident angle.

According to the first light receiving element 151 of the present embodiment, the first angle limiting filter 81 whose degree of angle limitation decreases toward the +X side away from the first light emitting element 50 is provided, such that it is possible to inject the scattering components LG1, which are blocked by the angle limiting filter of the related art, into the sensor 20. Thus, the first light receiving element 151 reduces variations in the amount of received light over the light receiving surface 20a of the sensor 20 to efficiently inject green light LG emitted from the light emitting unit 11 into the sensor 20, thus achieving high detection accuracy.

The second light receiving element 161 is configured similar to the first light receiving element 151.

The second light receiving element 161 has a plurality of light receiving regions including a first light receiving region IA21, a second light receiving region IB21, and a third light receiving region IC21. Hereinafter, the first light receiving region IA21, the second light receiving region IB21, and the third light receiving region IC21 are collectively referred to as "each of the light receiving regions IA21, IB21, and IC21" unless particularly specified.

Each of the light receiving regions IA21, IB21, and IC21 corresponds to a part of the light receiving surface 30a of the sensor 30 of the second light receiving element 161. The light receiving regions IA21, IB21, and IC21 are arranged on the light receiving surface 30a of the sensor 30 one by one on the +X side in this order.

The second angle limiting filter 91 is configured similar to the first angle limiting filter 81. The second angle limiting filter 91 includes a first limiting region 91A, a second limiting region 91B, and a third limiting region 91C. Hereinafter, the first limiting region 91A, the second limiting region 91B, and the third limiting region 91C are collectively referred to as "each of the limiting regions 91A, 91B, and 91C" unless particularly specified.

The limiting regions 91A, 91B, and 91C correspond respectively to the light receiving regions IA21, IB21, and IC21. In the detecting device 103 of the present embodiment, the degree of angle limitation of each of the limiting regions 91A, 91B, and 91C progressively decreases away from the light emitting elements 60 and 70.

The second angle limiting filter 91 includes a silicon oxide layer 94 and a plurality of light shielding walls (second light shielding walls) 95 embedded in the silicon oxide layer 94. In the second angle limiting filter 91, the plurality of light shielding walls 95 are provided on the light receiving regions IA21, IB21, and IC21 of the second light receiving element 161. The plurality of light shielding walls 95 include light shielding walls 95a, 95b, 95c, 95d, 95e, 95f, and 95g. The second angle limiting filter 91 is formed by embedding a plurality of light shielding walls 95 with different heights in the silicon oxide layer 24 through multiple steps into which a wiring forming process of a semiconductor process is divided, similar to the first angle limiting filter 81.

The light shielding wall 95a and the light shielding wall 95b are arranged in the X-axis direction in the first limiting region 91A. In the case of the present embodiment, the heights of the light shielding walls 95a and 95b are set to, for example, 4 µm.

The light shielding wall 95c and the light shielding wall 95d are arranged in the X-axis direction in the second limiting region 91B. In the case of the present embodiment, the heights of the light shielding walls 95c and 95d are set to, for example, 3 µm.

The light shielding wall 95e, the light shielding wall 95f, and the light shielding wall 95g are arranged in the X-axis direction in the third limiting region 91C. In the case of the present embodiment, the heights of the light shielding walls 95e, 95f, and 95g are set to, for example, 2 µm.

The X-axis intervals between adjacent ones of the light shielding walls 95a, 95b, 95c, 95d, 95e, 95f, and 95g are set to, for example, 3 µm.

In the case of the present embodiment, the degrees of angle limitation of the limiting regions 91A, 91B, and 91C are defined by the heights of light shielding walls arranged in the X-axis direction.

In the present embodiment, the height of the light shielding walls 95c and 95d arranged in the X-axis direction in the second limiting region 91B among the plurality of light shielding walls 95 is less than the height of the light shielding walls 95a and 95b arranged in the X-axis direction in the first limiting region 91A among the plurality of light shielding walls 95.

The height of the light shielding walls 95e, 95f, and 95g arranged in the X-axis direction in the third limiting region 91C among the plurality of light shielding walls 95 is also less than the height of the light shielding walls 95c and 95d arranged in the X-axis direction in the second limiting region 91B among the plurality of light shielding walls 95.

In the second angle limiting filter 91 of the present embodiment, the heights of light shielding walls arranged in the X-axis direction are adjusted as described above such that the degree of angle limitation (the allowable incident angle) of the second light receiving element 161 decreases toward the +X side away from the light emitting elements 60 and 70 as illustrated in FIG. 8.

In the case of the present embodiment, the degree of angle limitation of the first limiting region 91A in the second angle limiting filter 91 is smaller than the degree of angle limitation of the first limiting region 81A in the first angle limiting filter 81. Specifically, the height of the light shielding walls 95a and 95b arranged in the X-axis direction in the first limiting region 91A of the second light receiving element 161 is less than the height of the light shielding walls 85a and 85b arranged in the X-axis direction in the first limiting region 81A of the first light receiving element 151.

That is, the allowable incident angle of the first limiting region 91A in the second angle limiting filter 91 is larger than the allowable incident angle of the first limiting region 81A in the first angle limiting filter 81. Making the allowable incident angle of the first limiting region 91A located on the light emitting unit 11 side (the −X side) in the second angle limiting filter 91 larger relative to that of the first limiting region 81A in the first angle limiting filter 81 in this manner ensures that red light LR or near-infrared light LI that is incident at a larger angle with respect to the second light receiving element 161 can be incident on the light receiving surface 30a of the sensor 30 without being blocked.

According to the second light receiving element 161 of the present embodiment, the second angle limiting filter 91 whose degree of angle limitation decreases toward the +X side away from the light emitting elements 60 and 70 is provided, such that it is possible to inject the scattering components LR1 and LI1, which are blocked by the angle limiting filter of the related art, into the sensor 30.

Thus, the second light receiving element 161 reduces variations in the amount of received light over the light receiving surface 30a of the sensor 30 to efficiently inject red light LR or near-infrared light LI emitted from the light emitting unit 11 into the sensor 30, thus achieving high detection accuracy.

Similar to the detecting device 3 of the above embodiments, the detecting device 103 of the present embodiment can improve the detection accuracy of the light receiving unit 112 by increasing the amount of received light while increasing the S/N ratio as described above. Thus, the measuring device using the detecting device 103 according to the present embodiment can provide a biometric measuring device capable of highly accurate detection while reducing power consumption.

EXAMPLES

In order to demonstrate the effects of the detecting devices 3 and 103 of the above embodiments, the present inventor has simulated both the amount of light received by the light receiving element according to the distance from the light emitting unit and the light receiving rate of the light receiving element for a first example, a second example, and a comparative example that will be described below.

Specifically, the detecting device 3 of the first embodiment was used as the first example, the detecting device 103 of the second embodiment was used as the second example, and a detecting device using an angle limiting filter in which light shielding walls are embedded at equal intervals was used as the comparative example.

In the angle limiting filter of the detecting device of the comparative example, for example, the intervals between adjacent light shielding walls were set to 3 μm and the heights of the light shielding walls were set to 5 μm.

Figure 9:
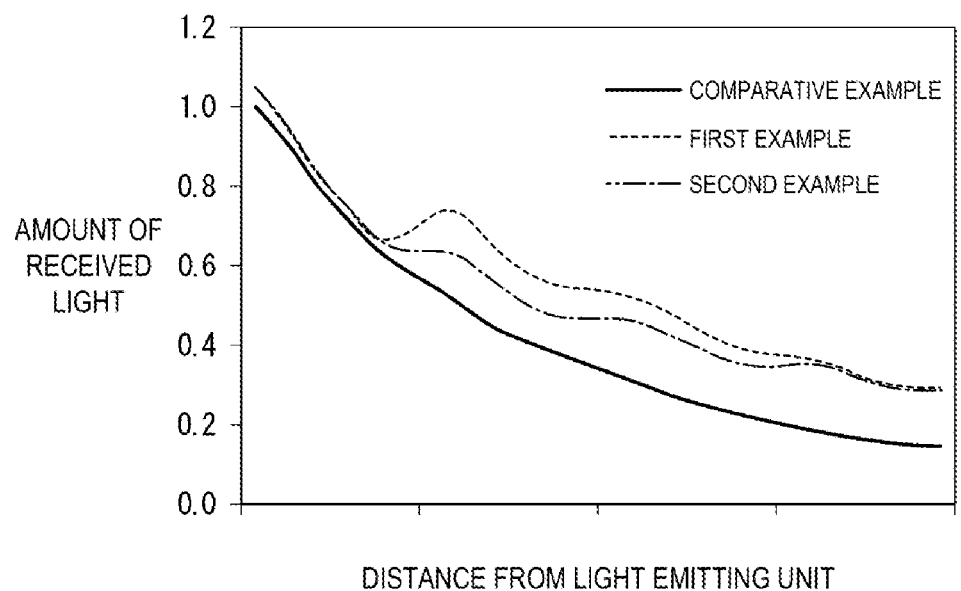
FIG. 9 is a graph showing simulation results of examples.

A graph of FIG. 9 shows the results of simulating the amount of light received by the light receiving element according to the distance from the light emitting unit for the detecting devices of the first example, the second example, and the comparative example. In FIG. 9, the horizontal axis of the graph represents the distance from the light emitting unit in the direction in which the light emitting unit and the light receiving unit are arranged (for example, the X-axis direction in FIG. 5) and the vertical axis of the graph represents the amount of light received by the light receiving element.

As shown in FIG. 9, it was confirmed that the amount of light received by the light receiving element increased as the distance from the light emitting unit increased in the detecting devices of the first and second examples, relative to the detecting device of the comparative example. That is, it was confirmed that the detecting devices of the first and second examples can make the amount of received light uniform over the surface of the light receiving element by decreasing the degree of angle limitation of the angle limiting filter as the distance from the light emitting unit increases.

Figure 10:
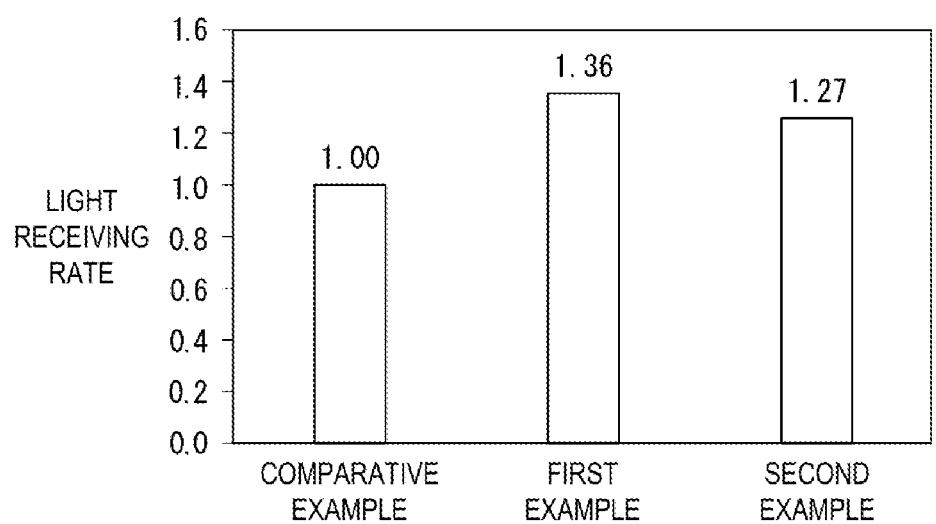
FIG. 10 is a graph showing simulation results of examples.

A graph of FIG. 10 shows the results of simulating the light receiving rate of the light receiving element for the detecting devices of the first example, the second example, and the comparative example. FIG. 10 shows the amount of received light for each of the detecting devices of the first and second examples when the amount of light received by the light receiving element of the detecting device of the comparative example is set to 1.0.

As shown in FIG. 10, it was confirmed that the detecting devices of the first and second examples can increase the amount of light received by the light receiving element to 1.36 or 1.27 relative to the detecting device of the comparative example.

From the results shown in FIGS. 9 and 10, it was confirmed that the detecting device of the first example has a higher effect of increasing the amount of light received by the light receiving element compared to the detecting device of the second example.

From the above, it has been demonstrated that the detecting devices 3 and 103 of the above embodiments can increase the amount of light received by each light receiving element, compared to the detecting device of the comparative example.

Although the present disclosure has been described above based on the above embodiments, the present disclosure is not limited to the above embodiments and can be implemented in various modes without departing from the spirit of the disclosure.

For example, although a living body is exemplified by a human in the above embodiments, the present disclosure can also be applied to measurement of the biological information (for example, pulse) of other animals.

Although the measuring device 100 of the first embodiment has been described with respect to the case where the detecting device 3 is provided in the main body 1 as an example, the installation location of the detecting device 3 is not limited to this, and for example, the detecting device 3 may be embedded in the back side of the belt.

Although the measuring device 100 of the first embodiment has been described with respect to a configuration in which it is of a wristwatch type as an example, the present disclosure can also be applied to, for example, a configuration in which it is worn on the subject's neck as a necklace type or a configuration in which it is attached to the subject's body as a sealed type, or a configuration in which it is attached to the subject's head as a head-mounted display type.

Although the detecting device 3 of the first embodiment has been described with respect to the case where the sensor 20 of the first light receiving element 51 includes four light receiving regions as an example, the number of light receiving regions is not limited to this. For example, the sensor 20 only needs to include at least two light receiving regions (the first light receiving region IA1 and the second light receiving region IB1) and may also include five or more light receiving regions. Similarly, the sensor 30 of the second light receiving element 61 only needs to include at least two light receiving regions (the first light receiving region IA2 and the second light receiving region IB2) and may also include five or more light receiving regions.

Although the detecting device 103 of the second embodiment has been described with respect to the case where the sensor 20 of the first light receiving element 151 includes three light receiving regions as an example, the sensor 20 of the first light receiving element 151 only needs to include at least two light receiving regions (the first light receiving region IA11 and the second light receiving region IB11) and may also include five or more light receiving regions. Similarly, the sensor 30 of the second light receiving element 161 only needs to include at least two light receiving regions (the first light receiving region IA21 and the second light receiving region IB21) and may also include five or more light receiving regions.

Although the detecting device 3 of the first embodiment has been described with respect to the case where each of the light emitting elements 50, 60, and 70 is caused to emit light in a time division manner as an example, the first light emitting element 50 may be constantly lit rather than being lit in a time division manner because the first light receiving element 51 corresponding to green light LG of the first light emitting element 50 is individually provided. Similarly, the first light emitting element 50 in the second embodiment may be constantly lit rather than being lit in a time division manner.

A detecting device of an aspect of the present disclosure may be configured as follows.

The detecting device of the aspect of the present disclosure includes a light emitting portion that emits light and a light receiving portion including an angle limiting member that limits an angle of incidence of light from the light emitting portion, wherein the light receiving portion has a first light receiving region and a second light receiving region that is spaced further from the light emitting portion than the first light receiving region is, the angle limiting member includes a first limiting region corresponding to the first light receiving region and a second limiting region corresponding to the second light receiving region, and a degree of angle limitation of the second limiting region is smaller than a degree of angle limitation of the first limiting region.

The detecting device of the aspect of the present disclosure may be configured such that, when a direction in which the light emitting portion and the light receiving portion are arranged is defined as a first direction, the angle limiting member includes a plurality of light shielding walls provided in the light receiving portion, and an interval in the first direction between adjacent light shielding walls in the second limiting region among the plurality of light shielding walls is larger than an interval in the first direction between adjacent light shielding walls in the first limiting region among the plurality of light shielding walls.

The detecting device of the aspect of the present disclosure may be configured such that the light emitting portion includes a first light emitting element configured to emit first light having a green wavelength band and a second light emitting element provided in a second direction intersecting the first direction with respect to the first light emitting element and configured to emit second light having a wavelength band longer than those of the green wavelength band, the light receiving portion includes a first light receiving element configured to receive the first light from the first light emitting element and a second light receiving element configured to receive the second light from the second light emitting element, and the first light receiving element is provided closer to the light emitting portion in the first direction than the second light receiving element is.

The detecting device of the aspect of the present disclosure may be configured such that the angle limiting member includes a first angle limiting filter configured to limit an angle of incidence of the first light with respect to the first light receiving element and a second angle limiting filter configured to limit an angle of incidence of the second light with respect to the second light receiving element, and a degree of angle limitation of the first limiting region in the second angle limiting filter is smaller than a degree of angle limitation of the first limiting region in the first angle limiting filter.

The detecting device of the aspect of the present disclosure may be configured such that the first angle limiting filter includes a plurality of first light shielding walls provided in the first light receiving element, the second angle limiting filter includes a plurality of second light shielding walls provided in the second light receiving element, and an interval in the first direction between adjacent ones of the second light shielding walls in the first limiting region of the second light receiving element is larger than an interval in the first direction between adjacent ones of the first light shielding walls in the first limiting region of the first light receiving element.

The detecting device of the aspect of the present disclosure may be configured such that, when a direction in which the light emitting portion and the light receiving portion are arranged is defined as a first direction, the angle limiting member includes a plurality of light shielding walls provided in the light receiving portion, and a height of the light shielding walls arranged in the first direction in the second limiting region is less than a height of the light shielding walls arranged in the first direction in the first limiting region.

The detecting device of the aspect of the present disclosure may be configured such that the light emitting portion includes a first light emitting element configured to emit first light having a green wavelength band and a second light emitting element provided in a second direction intersecting the first direction with respect to the first light emitting element and configured to emit second light having a wavelength band longer than those of the green wavelength band, the light receiving portion includes a first light receiving element configured to receive the first light from the first light emitting element and a second light receiving element configured to receive the second light from the second light emitting element, and the first light receiving element is provided closer to the light emitting portion in the first direction than the second light receiving element is.

The detecting device of the aspect of the present disclosure may be configured such that the angle limiting member includes a first angle limiting filter configured to limit an angle of incidence of the first light with respect to the first light receiving element and a second angle limiting filter configured to limit an angle of incidence of the second light with respect to the second light receiving element, and a degree of angle limitation of the first limiting region in the second angle limiting filter is smaller than a degree of angle limitation of the first limiting region in the first angle limiting filter.

The detecting device of the aspect of the present disclosure may be configured such that the first angle limiting filter includes a plurality of first light shielding walls provided in the first light receiving element, the second angle limiting filter includes a plurality of second light shielding walls provided in the second light receiving element, and a height of the second light shielding walls arranged in the first direction in the first limiting region of the second light receiving element is less than a height of the first light shielding walls arranged in the first direction in the first limiting region of the first light receiving element.

The detecting device of the aspect of the present disclosure may be configured such that the light receiving portion further includes a third light receiving region that is spaced further from the light emitting portion than the second light receiving region is, and the angle limiting member further includes a third limiting region corresponding to the third light receiving region and having a smaller degree of angle limitation than the second limiting region.

A detecting device of an aspect of the present disclosure may be configured as follows.

The detecting device of the aspect of the present disclosure includes a light emitting portion configured to emit light to a living body, a light receiving portion arranged in a first direction with respect to the light emitting portion and configured to receive light from the living body, and a plurality of light shielding walls arranged in the first direction and configured to limit an angle of incidence of light on the light receiving portion, wherein an interval between the light shielding walls in a region far from the light emitting portion is larger than an interval between the light shielding walls in a region close to the light emitting portion.

A measuring device of an aspect of the present disclosure may be configured as follows.

The measuring device of the aspect of the present disclosure includes the detecting device according to the above aspect and an information analysis unit configured to identify biological information from a detection signal indicating a detection result of the detecting device.

What is claimed is:

1. A detecting device comprising:
   a light source that emits a light; and
   a light receiving unit that includes:
      a sensor having a first light receiving region and a second light receiving region farther away from the light source than the first light receiving region, and
      an angle limiting member having a first limiting region corresponding to the first light receiving region and a second limiting region corresponding to the second light receiving region,
   wherein a degree of angle limitation of the second limiting region is smaller than a degree of angle limitation of the first limiting region,
   wherein, when a direction in which the light source and the light receiving unit are aligned is defined as a first direction, the angle limiting member includes a plurality of light shielding walls provided at the light receiving unit, and a height of the light shielding walls aligned in the first direction in the second limiting region is less than a height of the light shielding walls aligned in the first direction in the first limiting region.

2. The detecting device according to claim 1, wherein the light receiving unit further includes a third light receiving region that is located further away from the light source than the second light receiving region, and the angle limiting member includes a third limiting region corresponding to the third light receiving region and having a smaller degree of angle limitation than the second limiting region.

3. The detecting device according to claim 1, wherein the light source includes a first light emitting element configured to emit first light and a second light emitting element provided in a second direction intersecting the first direction and configured to emit second light having a wavelength band longer than a wavelength band of the first light, the light receiving unit includes a first light receiving element configured to receive the first light from the first light emitting element and a second light receiving element configured to receive the second light from the second light emitting element, and the first light receiving element is closer to the light source in the first direction than the second light receiving element, wherein each of the first and second light receiving elements includes a sensor.

4. The detecting device according to claim 3, wherein the angle limiting member includes a first angle limiting filter configured to limit an angle of incidence of the first light with respect to the first light receiving element, and a second angle limiting filter configured to limit an angle of incidence of the second light with respect to the second light receiving element, and a degree of angle limitation of the first limiting region in the second angle limiting filter is smaller than a degree of angle limitation of the first limiting region in the first angle limiting filter.

5. The detecting device according to claim 4, wherein the first angle limiting filter includes a plurality of first light shielding walls provided at the first light receiving element, the second angle limiting filter includes a plurality of second light shielding walls provided at the second light receiving element, and a height of the second light shielding walls aligned in the first direction in the first limiting region of the second light receiving element is less than a height of the first light shielding walls aligned in the first direction in the first limiting region of the first light receiving element.

6. The detecting device according to claim 1, wherein, when a direction in which the light source and the light receiving unit are aligned is defined as a first direction, the angle limiting member includes a plurality of light shielding walls provided at the light receiving unit, and a distance in the first direction between adjacent light shielding walls of the plurality of light shielding walls in the second limiting region is larger than a distance in the first direction between adjacent light shielding walls of the plurality of light shielding walls in the first limiting region.

7. The detecting device according to claim 6, wherein the light source includes a first light emitting element configured to emit first light, and a second light emitting element provided in a second direction intersecting the first direction and configured to emit second light having a wavelength band longer than a wavelength band of the first light, the light receiving unit includes a first light receiving element configured to receive the first light from the first light emitting element, and a second light receiving element configured to receive the second light from the second light emitting element, and the first light receiving element is closer to the light source in the first direction than the second light receiving element, wherein each of the first and second light receiving elements includes a sensor.

8. The detecting device according to claim 7, wherein the angle limiting member includes a first angle limiting filter configured to limit an angle of incidence of the first light with respect to the first light receiving element, and a second angle limiting filter configured to limit an angle of incidence of the second light with respect to the second light receiving element, and a degree of angle limitation of the first limiting region in the second angle limiting filter is smaller than a degree of angle limitation of the first limiting region in the first angle limiting filter.

9. The detecting device according to claim 8, wherein the first angle limiting filter includes a plurality of first light shielding walls provided at the first light receiving element, the second angle limiting filter includes a plurality of second light shielding walls provided at the second light receiving element, and a distance in the first direction between adjacent second light shielding walls, of the plurality of second light shielding walls, in the first limiting region of the second light receiving element is larger than a distance in the first direction between adjacent first light shielding walls, of the plurality of first light shielding walls, in the first limiting region of the first light receiving element.

10. A measuring device comprising:
the detecting device according to claim 1; and
a control device configured to identify biological information from a detection signal indicating a result of detection by the detecting device.

11. A detecting device comprising:
a light source that emits a light to a living body;
a light receiving unit that is aligned in a first direction with respect to the light source and that receives the light from the living body; and
a plurality of light shielding walls that are aligned in the first direction and that limit an angle of incidence of light on the light receiving unit, wherein a distance between the light shielding walls in a region far from the light source is larger than a distance between the light shielding walls in a region close to the light source, wherein, when a direction in which the light source and the light receiving unit are aligned is defined as a first direction, and a height of the light shielding walls aligned in the first direction in the region far from the light source is less than a height of the light shielding walls aligned in the first direction in the region close to the light source.

* * * * *